(12) United States Patent
Hutàs

(10) Patent No.: US 7,588,787 B2
(45) Date of Patent: Sep. 15, 2009

(54) MEDICATED PRODUCTION FOR LOCAL USE BASED ON NATURAL MATERIALS

(76) Inventor: István Hutàs, 10 Szijgyártó u., Budapest (HU) H-1048

(*) Notice: Subject to any disclaimer, the term of this patent is extended or adjusted under 35 U.S.C. 154(b) by 0 days.

(21) Appl. No.: 11/908,700

(22) PCT Filed: May 25, 2006

(86) PCT No.: PCT/HU2006/000048
§ 371 (c)(1), (2), (4) Date: Sep. 14, 2007

(87) PCT Pub. No.: WO2006/126034
PCT Pub. Date: Nov. 30, 2006

(65) Prior Publication Data
US 2008/0145456 A1  Jun. 19, 2008

(30) Foreign Application Priority Data
May 25, 2005 (HU) .................. 0500530

(51) Int. Cl.
*A61K 36/53* (2006.01)
(52) U.S. Cl. .................. 424/736; 424/745; 424/764
(58) Field of Classification Search .......... None
See application file for complete search history.

(56) References Cited

U.S. PATENT DOCUMENTS

| | | | |
|---|---|---|---|
| 4,316,887 A | 2/1982 | Kamishita et al. | |
| 5,853,768 A | 12/1998 | Altadonna et al. | |
| 6,613,755 B2* | 9/2003 | Peterson et al. | 514/63 |
| 6,616,922 B2* | 9/2003 | Taylor et al. | 424/70.28 |
| 6,884,763 B2* | 4/2005 | Willard et al. | 510/136 |
| 2004/0059281 A1* | 3/2004 | Saemundsdottir | 604/11 |

FOREIGN PATENT DOCUMENTS

| | | |
|---|---|---|
| HU | 200273 B | 5/1990 |
| HU | 207446 B | 12/1991 |
| WO | WO 00/42848 A | 7/2000 |

OTHER PUBLICATIONS

Gizella Petri: Phitoterahy In The Medical Practice, Springer, 1999, pp. 216-217.
Hustas Istvan et al., Method for Producing Medicinal Preparation of Local Use, Partial translation of cover page of Hungary Patent No. 207446 published Dec. 30, 1991, p. 1.
Wessely, Antal et al., Preparation of meat product by which a meat mass is frozen into slabs that are sawn into portions for subsequent packaging, Partial translation of Hungary Patent No. 200273 grant date May 28, 1990, p. 1.
Gulya,Ernoe et al., Curative Analgetic Compositions, Abstract of Hungary Patent No. 98 02893 published Sep. 28, 2000, pp. 1-2.
Hungary Patent Office, Search Report for Hungary Patent No. P0500530, dated Jun. 15, 2006, p. 1.

* cited by examiner

*Primary Examiner*—Susan C Hoffman
(74) *Attorney, Agent, or Firm*—Millen, White, Zelano & Branigan, P.C.

(57) ABSTRACT

The subject of the invention is a medicated product for local use based on natural materials which said product is suitable for alleviating respectively eliminating pain of different locomotor complaints of the body applying the product through the skin surface. The product according to the invention contains menthol in water solution, ethylene-diamine-tetra-acetic acid-alkali metal, salt (EDTA), furthermore in given case it contains carrier, diluter and/or other auxiliary substances applied in producing products for local use, characterized by that, the product contains essential oils furthermore non-ionic surface-active emulsifying agent and substances in the composition of the product as follows: Aethereum gerani 0.1 . . . 3 mass %, preferably 1.5 mass %, Aethereum rosmarini 0.1 . . . 2 mass %, preferably 0.5 mass %, Aethereum citri 0.5 . . . 3 mass %, preferably 1 mass %, Mentholum 0.1 . . . 3 mass %, preferably 1 mass %, EDTA 2Na 1 . . . 6 mass %, preferably 3 mass %.

19 Claims, No Drawings

MEDICATED PRODUCTION FOR LOCAL USE BASED ON NATURAL MATERIALS

The subject of the invention is a medicated product for local use based on natural materials which said product is suitable for alleviating respectively eliminating pain of different locomotor complaints of the body applying the product through the skin surface.

In the state of the art there are various products to treat the locomotor complaints of the old age and to restore the body. HU 207 446 Patent describes a method for producing a solid ointment, gel and hydro-solid stift to treat pain caused especially by hardening of the arteries due to the aging sclerotic process of reumatic, degenerative and post-trauma features. In this method ethylene-diamine-tetra-acetic acid-sodium salt, camphor, menthol, if necessary a drug against inflammation, preferably ethylenglycol-salicilate, anaesthetic, preferably prokain, anti-oxydant, glutation together with the carrier materials usually applied in producing ointments, preferably hydroxy-methyl-cellulose, glycerine and conserving agent mixed in an aqueous media and form it into a hydro-gel or ointment and transform it furthermore into a hydro solid stift.

The deficiency of the products in the state of the art is, that the sclerotic processes of the old age are partly treated one-sidedly and their active materials must be most of the time supplemented by other drugs.

When working out the solution according to the invention our aim was to make a product which using natural materials without applying chemicals and drugs makes possible to alleviate respectively eliminate symptoms of disorders of aging of the locomotor system respectively contribute to the efficient supplementation of treatments and massages in physiotherapy.

When elaborating the solution according to the invention we realized, that in case we make a homogenous gel texture product consisting of natural essential oils, furthermore of active materials of essential oils and other additives, then the set aim can be achieved.

The invention is a medicated product for local use based on natural materials, said product contains menthol in water solution, ethylene-diamine-tetra-acetic acid-alkali metal salt (EDTA), furthermore in given case it contains carrier, diluter and/or other auxiliary substances applied in producing products for local use, characterized by that, the product contains essential oils furthermore non-ionic surface-active emulsifying agent and substances in the composition of the product as follows:

| | |
|---|---|
| Aethereum gerani | 0.1 . . . 3 mass %, preferably 1.5 mass %, |
| Aethereum rosmarini | 0.1 . . . 2 mass %, preferably 0.5 mass %, |
| Aethereum citri | 0.5 . . . 3 mass %, preferably 1 mass % |
| Mentholum | 0.1 . . . 3 mass %, preferably 1 mass %, |
| EDTA 2Na | 1 . . . 6 mass %, preferably 3 mass %. |

In one of preferred realization of the product according to the invention, the non-ionic emulsifying agent used in the product is in given case polysorbate or berol, or NPC-6 (sodium polyacrylate and hydrogenated polydecene and trideceth-6, or carbopol and the proportion of solvent in the composition of the product is 0.4 . . . 10 mass %.

In another preferred realization of the product according to the invention, the product contains 0.1 . . . 3 mass %, preferably 1 mass % Aethereum oregani.

In a further preferred realization of the product according to the invention, the product contains 0.1 . . . 3 mass %, preferably 1 mass % Aethereum thymi.

In a further preferred realization of the product according to the invention, the product contains 0.1 . . . 5 mass %, preferably 1.5 mass % Champhorum.

In a further preferred realization of the product according to the invention, the product contains 0.01 . . . 1 mass %, preferably 0.25 mass % Aethereum chamomillae.

In a further preferred realization of the product according to the invention, the product contains 0.5 . . . 6 mass % gel-composer, preferably 3.5 mass % Hydroxiaethilcellulose.

In a further preferred realization of the product according to the invention, the product contains 0.001 . . . 0.05 mass % coloring agent, in given case 0.025 mass % methylene blue or 0.01 mass % carotine.

In a further preferred realization of the product according to the invention, the product to be applied for massage contains 0.5 . . . 10 mass % natural cosmetic oil of natural vegetable raw material, preferably 5 mass % linseed oil.

In a further preferred realization of the product according to the invention the aqueous media of the solution contains alcohol, preferably 5-10 mass % 1-2 propane-diol.

The solution according to the invention will be set forth furthermore by the examples of application as follows:

EXAMPLE 1

Basic Composition (Minimum Components Without Coloring)

Universal Minimum Healing Effect as Well as a Cosmetic

| | |
|---|---|
| Aethereum gerani | 1.00 g |
| Aethereum rosmarini | 0.50 g |
| Aethereum citri | 0.50 g |
| Mentholum | 1.00 g |
| Karbopol | 6.00 g |
| EDTA 2Na | 3.00 g |
| Aqua destillata ad | 100.00 g |

EXAMPLE 2

Product Used with Massage

| | |
|---|---|
| Aethereum gerani | 1.00 g |
| Aethereum rosmarini | 0.50 g |
| Aethereum citri | 0.50 g |
| Mentholum | 1.00 g |
| Polisorbat 20 | 6.00 g |
| EDTA 2Na | 3.00 g |
| NPC-6 | 3.50 g |
| Linseed oil | 5.00 g |
| Aqua destillata ad | 100.00 g |

EXAMPLE 3

| | |
|---|---|
| *Aethereum gerani* | 1.50 g |
| *Aethereum rosmarini* | 0.50 g |
| *Aethereum citri* | 0.50 g |
| *Aethereum thymi* | 1.00 g |
| *Aethereum chamomillae* | 0.025 g |
| Mentholum | 1.00 g |
| Champhorum | 1.50 g |
| EDTA 2Na | 3.00 g |
| Karbopol | 6.00 g |
| Aqua destillata ad | 100.00 g |

EXAMPLE 4

| | |
|---|---|
| *Aethereum gerani* | 1.50 g |
| *Aethereum rosmarini* | 0.50 g |
| *Aethereum citri* | 1.00 g |
| *Aethereum oregani* | 1.00 g |
| *Aethereum chamomillae* | 0.025 g |
| Mentholum | 1.00 g |
| Champhorum | 1.50 g |
| Polisorbat 20 | 4.00 g |
| Karbopol | 5.00 g |
| EDTA 2Na | 3.00 g |
| Aqua destillata ad | 100.00 g |

EXAMPLE 5

| | |
|---|---|
| *Aethereum gerani* | 1.50 g |
| *Aethereum rosmarini* | 0.50 g |
| *Aethereum citri* | 1.00 g |
| *Aethereum oregani* | 1.00 g |
| *Aethereum chamomillae* | 0.025 g |
| Mentholum | 1.00 g |
| Champhorum | 1.50 g |
| Berol | 6.00 g |
| EDTA 2Na | 3.00 g |
| Hydroxiaethilcellulose | 3.50 g |
| Aqua destillata ad | 100.00 g |

EXAMPLE 6

| | |
|---|---|
| *Aethereum gerani* | 1.50 g |
| *Aethereum rosmarini* | 0.50 g |
| *Aethereum citri* | 1.00 g |
| *Aethereum oregani* | 1.00 g |
| *Aethereum chamomillae* | 0.025 g |
| Mentholum | 1.00 g |
| Champhorum | 1.50 g |
| Karbopol | 4.00 g |
| Polisorbat 20 | 3.00 g |
| EDTA 2Na | 3.00 g |
| Hydroxiaethilcellulose | 3.50 g |
| Methylene blue | 0.025 g |
| Aqua destillata ad | 100.00 g |

The advantage of the solution according to the invention is, that the effect of regeneration, alleviating inflammation is achieved by the use of essential oils of natural source instead of drugs. These do not irritate the skin, but protect it, keep it subtle, keep pH of skin on an optimal level, hydrate the skin and increase its ability of conductivity, keep it antiseptic, protect it against fungus infection especially in periods after bath.

An additional advantage of the solution according to the invention is, that it can be easily applied on the body surface to be treated without experiencing greasy, sticky effect, and the layer of film created this way on the skin does not prevent the skin from breathing. The product has an advantageous effect on the skin itself as well, as it influences the skin with keeping the natural pH value and the stretch of the skin.

The components applied in the product according to the invention are essential oils of natural origin, respectively extracts of essential oils do not irritate the skin in the applied concentration and composition. The components have strong and durable anti-oxidant and radical scavenger effect, which spread below the area of the skin.

The invention claimed is:

1. A pharmaceutical composition suitable for local use comprising about
   0.1 to 3 mass % of Aethereum gerani,
   0.1 to 2 mass % of Aethereum rosmarini,
   0.5 to 3 mass % of Aethereum citri,
   0.1 at 3 mass % of Mentholum, and
   1 to 6 mass % of EDTA 2Na, and optionally one or more carriers, diluents, auxiliary substances, menthol in water solution, an essential oil, and a non-ionic surface-active emulsifying agent.

2. A pharmaceutical composition according to claim 1, comprising about 1.5 mass % of Aethereum gerani.

3. A pharmaceutical composition according to claim 1, comprising about 0.5 mass % of Aethereum rosmarini.

4. A pharmaceutical composition according to claim 1, comprising about 1 mass % of Aethereum citri.

5. A pharmaceutical composition according to claim 1, comprising about 1 mass % of Mentholum.

6. A pharmaceutical composition according to claim 1, comprising about 3 mass % of EDTA 2Na.

7. A pharmaceutical composition according to claim 1, comprising about
   1.5 mass % of Aethereum gerani,
   0.5 mass % of Aethereum rosmarini,
   1 mass % of Aethereum citri,
   1 mass % of Mentholum, and
   3 mass % of EDTA 2Na.

8. A pharmaceutical composition according to claim 1, wherein the non-ionic emulsifying agent is polysorbate, berol, carbopol or a composition comprising sodium polyacrylate and hydrogenated polydecene and trideceth-6.

9. A pharmaceutical composition according to claim 1, which comprises a solvent at about 0.4 to 10 mass %.

10. A pharmaceutical composition according to claim 1, further comprising about 0.1 to 3 mass % Aethereum oregani.

11. A pharmaceutical composition according to claim 1, further comprising about 0.1 to 3 mass % Aethereum thymi.

12. A pharmaceutical composition according to claim 1, further comprising about 0.1 to 5 mass % Champhorum.

13. A pharmaceutical composition according to claim 1, further comprising about 0.01 to 1 mass % Aethereum chamomillae.

14. A pharmaceutical composition according to claim 1, further comprising about 0.5 to 6 mass % of a gel-composer.

15. A pharmaceutical composition according to claim 1, further comprising one or more of
   (a) 0.001 to 0.05 mass % of a coloring agent,
   (b) 0.5 to 10 mass % of a natural cosmetic oil of a natural vegetable raw material, or
   (c) an alcohol.

16. A pharmaceutical composition according to claim 15, comprising 0.5 to 10 mass % of linseed oil.

17. A method for alleviating or eliminating pain that is different from a locomotor complaint of the body comprising applying the pharmaceutical composition of claim 1 to the skin surface of a subject in need thereof.

18. A method for massage therapy comprising applying the pharmaceutical composition of claim 1 to the skin surface of a subject undergoing message therapy.

19. A method for alleviating inflammation comprising applying the pharmaceutical composition of claim 1 to the skin surface of a subject in need thereof.

* * * * *